United States Patent
Strebelle et al.

(12) 
(10) Patent No.: US 6,288,248 B1
(45) Date of Patent: Sep. 11, 2001

(54) EPICHLOROHYDRIN-BASED PRODUCT AND PROCESS FOR MANUFACTURING THIS PRODUCT

(75) Inventors: Michel Strebelle, Brussels; Patrick Gilbeau, Braine-le-Comte; Jean-Pierre Catinat, Waudrez, all of (BE)

(73) Assignee: Solvay (Société Anonyme), Brussels (BE)

( * ) Notice: Subject to any disclaimer, the term of this patent is extended or adjusted under 35 U.S.C. 154(b) by 0 days.

(21) Appl. No.: 09/199,570

(22) Filed: Nov. 25, 1998

(30) Foreign Application Priority Data

Nov. 27, 1997 (BE) .................................................. 09700961

(51) Int. Cl.7 ........................ C07D 301/12; C07D 301/06
(52) U.S. Cl. ........................ 549/518; 549/516; 549/524; 549/525
(58) Field of Search .................................. 549/516, 524, 549/525, 518

(56) References Cited

U.S. PATENT DOCUMENTS 4,424,391 * 1/1984 Walraevens et al. ................. 549/525
5,169,964 * 12/1992 Jacobson et al. .................... 549/541
5,344,945 * 9/1994 Grunchard Frans ................ 549/521
5,354,875 * 10/1994 Nemeth et al. ...................... 549/531

FOREIGN PATENT DOCUMENTS

| 1 100 119 A1 | 7/1983 | (EP) . |
| 0 230 949 A2 | 1/1987 | (EP) . |
| 0230949 * | 8/1987 | (EP) . |
| 0 366 077 A1 | 2/1989 | (EP) . |
| 0 368 656 A2 | 11/1989 | (EP) . |
| 0 568 336 A2 | 4/1993 | (EP) . |

\* cited by examiner

*Primary Examiner*—Alan L. Rotman
*Assistant Examiner*—Rita Desai
(74) *Attorney, Agent, or Firm*—Marina V. Schneller; Venable

(57) ABSTRACT

Epichlorohydrin-based product containing at least 99.9% by weight of epichlorohydrin and a total amount of chloro impurities of less than or equal to 150 ppm by weight, and process for manufacturing this product by reaction of allyl chloride with a peroxide compound in the presence of water, a catalyst and a diluent in at least one reactor, and separation of the epichlorohydrin formed.

24 Claims, No Drawings

EPICHLOROHYDRIN-BASED PRODUCT AND PROCESS FOR MANUFACTURING THIS PRODUCT

The present invention relates to an epichlorohydrin-based product and to a process for manufacturing an epichlorohydrin-based product by reaction between allyl chloride and a peroxide compound in a liquid medium containing a diluent, and more particularly to an epichlorohydrin-based product which is depleted in chloro impurities and to an improved process for manufacturing this product which is depleted in chloro impurities.

It is well known to prepare epichlorohydrin by dehydrochiorination, using a basic compound, of an aqueous solution of dichloropropanols, which is obtained by reacting, in a suitable reaction zone, allyl chloride, water and chlorine, as described, for example, in patent application EP-A-1,561, 441.

During this known process, unwanted by-products are generally formed, namely organochlorine products. Since these products are difficult to remove, some can be found in the epichlorohydrin. Furthermore, these by-products pose problems of disposal since they contribute towards the chemical oxygen demand and, where appropriate, to the presence of undesirable halo compounds.

The invention is directed towards overcoming the drawbacks of this known process for preparing epichlorohydrin by providing a purer product containing fewer impurities and especially fewer chloro impurities, as well as a simple process for preparing epichlorohydrin which generates fewer by-products and especially fewer chloro by-products and which exhibits high selectivity.

Consequently, the invention relates to an epichlorohydrin-based product containing at least 99.9% by weight of epichlorohydrin and a total amount of chloro impurities of less than or equal to 150 ppm by weight, in particular less than or equal to 100 ppm. This product advantageously contains an amount of methyl glycidyl ether of less than or equal to 250 ppm by weight, in particular less than or equal to 200 ppm. It preferably contains an amount of 2-methoxy-1-propanol of less than or equal to 100 ppm by weight, in particular less than or equal to 80 ppm.

The expression impurities and by-products is understood to denote products which are formed by reaction between epichlorohydrin and water or optionally the diluent and by reaction between allyl chloride and the diluent. For example, epichlorohydrin and the water or the methanol used as diluent can form, under the usual epoxidation conditions, appreciable amounts of 1-chloro-3-methoxy-2-propanol, 1-chloro-2-methoxy-3-propanol, 1,3-dichloro-2-propanol, 2,3-dichloropropanol and 1-chloro-2,3-dihydroxypropane. Moreover, the reaction between allyl chloride and the methanol used as diluent can give methyl allyl ether which, under the conditions of epoxidation with a peroxide compound such as hydrogen peroxide, can give methyl glycidyl ether. Products formed by reaction between water or the diluent and side products which may be present in the starting allyl chloride can also be found among the impurities and by-products. This is the case, for example, for 2-methoxy-1-propanol.

The invention also relates to a process for manufacturing an epichlorohydrin-based product containing at least 99.9% by weight of epichlorohydrin and a total amount of chloro impurities of less than or equal to 150 ppm by weight, in which (a) allyl chloride is reacted with a peroxide compound in the presence of water, a catalyst and a diluent in at least one reactor, and (b) the reaction mixture leaving step (a) is subjected to a treatment to separate out the epichlorohydrin.

The catalysts which can be used in step (a) of the process according to the invention are preferably titanium silicalite type catalysts. These are crystalline synthetic materials similar in structure to zeolites, comprising silicon oxide and titanium oxide and characterized by an infrared absorption band at about 950 –960 cm$^{-1}$. Their general formula is typically:

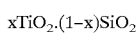

$xTiO_2.(1-x)SiO_2$ in which x is between 0.0001 and 0.5, preferably between 0.001 and 0.05.

The materials of this type, known as TS-1, have a microporous crystalline zeolite structure similar to that of zeolite ZSM-5. The properties and the main uses of these compounds are known (B. Notari, Structure-Activity and Selectivity Relationship in Heterogeneous Catalysis, R. K. Grasselli and A. W. Sleight Editors, Elsevier, 1991, pp. 243–56). Their synthesis has been studied in particular by A. Van der Poel and J. Van Hooff(Applied Catalysis A, 1992, Vol. 92, pp. 93–111). Other materials of this type have a structure similar to that of beta-zeolite or zeolite ZSM-11.

The catalyst are generally in amounts of greater than 2, usually greater than 5 and preferably greater than 10 g per kilo of reation mixture. These amounts generally do not exceed 200 and preferably not 100 g per kilo of reaction mixture.

The peroxide compound which can be used in step (a) of the process according to the invention can be chosen from hydrogen peroxide and any peroxide compound containing active oxygen and capable of carrying out an epoxidation. Examples which may be mentioned are the peroxide compounds obtained by oxidation of organic compounds such as ethylbenzene, isobutane and isopropanol. Hydrogen peroxide is preferred.

The peroxide compound can be used in the form of an aqueous solution or in the form of an organic solution. For economic reasons, it is generally used in the form of an aqueous solution.

When the peroxide compound is hydrogen peroxide, solutions containing at least 20% and preferably at least 30% by weight of hydrogen peroxide are particularly suitable. The solutions used can contain up to 85% by weight of hydrogen peroxide. Preferably, solutions containing less than 40% by weight of hydrogen peroxide are used. It is particularly preferred to use solutions containing about 35% by weight of hydrogen peroxide.

The process in step (a) may be performed with an allyl chloride/peroxide compound molar ratio which can vary within a wide range. The molar ratio is generally at least 0.5, in particular at least 1. The molar ratio is usually less than or equal to 10, in particular to 4.

The poor miscibility of the reagents, the allyl chloride and the aqueous solution of peroxide compound makes it necessary to use a common diluent in step (a). The diluent used in step (a) of the process according to the invention can be chosen from any organic solvent which is at least partially water-soluble. Solvents which are particularly suitable are alcohols. The preferred alcohols contain from 1 to 5 carbon atoms and comprise only one —OH group. Examples which may be mentioned are methanol, ethanol, n-propanol, isopropanol, n-butanol, isobutanol, s-butanol t-butanol and pentanol. Usually, the alcohol is methanol or t-butanol. Methanol is particularly preferred.

The diluent can be used in variable amounts. In general, the reaction mixture contains at least 30% by weight of diluent, usually at least 50% by weight. It commonly contains not more than 90% by weight of diluent. Preferably, it contains not more than 75% by weight of diluent.

The temperature and pressure at which step (a) is carried out can vary within very wide ranges. They are chosen so as not to exceed the decomposition temperature of the reaction mixture.

The temperature of step (a) is commonly less than 150° C. and usually between 0 and 120° C. Good results have been obtained at temperatures of between 20 and 80° C.

The pressure in step (a) can be less than, equal to or greater than atmospheric pressure. The pressure is generally less than 5 bar. Good results have been obtained using pressures of from 0.05 to 3 bar.

The duration of step (a) depends on the catalyst, the peroxide compound, the diluent and the amounts of each of the constituents used. It is chosen so as to obtain a very high to quantitative degree of conversion of the peroxide compound. It can range from 1 minute to 50 hours. Good results have been obtained with a reaction time of from 5 minutes to 2 hours.

Step (a) can be carried out in a single reactor or in a series of reactors in parallel or in series. Any type of apparatus which is suitable for liquid reaction mixtures can be used to carry out step (a) of the process according to the invention. It is thus possible, for example, to use one or more reactor(s) in a fixed bed, in a mobile bed, in a stirred bed or in a fluidized bed. Preferably, one or more reactor(s) in series will be used, in which reactor(s) the catalyst is maintained in suspension by fluidization. It is particularly preferred to use at least three reactors in series.

The reaction is exothermic. The heat of reaction can be removed from each reactor by circulating the reaction mixture over a cooling unit.

The catalyst used in step (a) can be separated from the reaction mixture by a suitable method such as filtration. It may be economically advantageous to re-use the recovered catalyst in subsequent epoxidation reactions. In order to be able to re-use the catalyst, it is advantageous to regenerate it by a technique such as calcination, treatment with a solvent or placing in contact with a liquid solution comprising at least one oxidizing agent such as hydrogen peroxide, ozone or an organic peroxide compound such as performic acid or peracetic acid.

The reaction mixture leaving step (a) generally contains at least 1% by weight of epichlorohydrin, usually at least 5% by weight.

It commonly contains not more than 50% by weight of epichlorohydrin. Preferably, it contains not more than 20% of epichlorohydrin.

Typically, the reaction mixture leaving step (a) contains from 5 to 25% of water.

The content of unconverted allyl chloride in the reaction mixture leaving step (a) is generally from 5 to 20% by weight.

The treatment (b) to separate out the epichlorohydrin can be carried out by standard separation methods such as extraction or distillation. In particular, the epichlorohydrin separation treatment (b) can be carried out by extraction using an extraction solvent.

The extraction solvent which can be used in step (b) can contain one or more compounds. Advantageously, an extraction solvent which dissolves epichlorohydrin well and in which the diluent is sparingly soluble is used. Preferably, an extraction solvent which also dissolves the starting allyl chloride well is used.

Compounds which can be used as extraction solvent in the epichlorohydrin separation treatment (b) are aliphatic or cyclic, linear or branched, optionally halogenated, saturated hydrocarbons comprising from 3 to 20 carbon atoms. Examples which may be mentioned in particular are n-decane, n-tridecane, 1,2,3-trichloropropane and decalin (decahydronaphthalene).

The extraction solvent for step (b) can also be chosen from optionally halogenated, unsaturated hydrocarbons comprising from 3 to 20 carbon atoms. One example which may be mentioned is allyl chloride.

Other compounds which can be used as extraction solvent in step (b) are aromatic hydrocarbons optionally containing alkyl, halo and/or nitrogenous substituents, comprising from 6 to 12 carbon atoms. Examples which may be mentioned are o-, m- and p-xylenes, 1,3,5-trimethylbenzene (mesitylene), o-, m- and p-dichlorobenzenes, o-, m- and p-chlorotoluenes and nitrobenzene.

It may be advantageous in step (b) to use a mixture of at least two different solvents. These may be, for example, mixtures of an aromatic hydrocarbon as described above with an aliphatic hydrocarbon as described above. Other mixtures which may be suitable are mixtures of aliphatic hydrocarbons and mixtures of aromatic hydrocarbons.

Extraction solvents which give particularly high-quality performance in step (b) contain at least one compound chosen from o-dichlorobenzene, m-dichlorobenzene, 1,3,5-trimethylbenzene, decalin, o-chlorotoluene, 1,2,3-trichloropropane, allyl chloride, nitrobenzene and n-decane, and mixtures thereof Extraction solvents containing o-dichlorobenzene are most particularly preferred.

An extract containing at least some of the extraction solvent, at least 10% of the epichlorohydrin produced, possibly an excess of allyl chloride and traces of the diluent, on the one hand, and a raffinate containing at least some of the diluent, at least some of the water, and traces of epichlorohydrin and of by-products, on the other hand, are collected after extraction in step (b). The said extract and the said raffinate can then be treated separately.

The extract can thus be subjected to a distillation treatment (c) in order to separate a first fraction containing the epichlorohydrin produced, the excess allyl chloride, if any, and traces of diluent from a second fraction containing the extraction solvent, which is recycled into the extraction step (b).

The first fraction obtained in the distillation step (c) can then be subjected to a distillation treatment (d) in order to remove the excess allyl chloride, if any, and the traces of diluent, which are recycled into the epoxidation step (a). An epichlorohydrin-based product is then collected, which can be dried in an azeotropic column.

Similarly, the raffinate obtained in the extraction step (b) can be subjected to a distillation (e) in order to separate a first fluid containing the water and by-products from a second fluid containing the diluent and the traces of epichlorohydrin, which are recycled into the epoxidation step (a).

The first fluid can then be subjected to a purification treatment (f) in order to remove the by-products. The purification treatment (f) can be carried out by distillation in the presence of an organic compound or by extraction using an extraction liquid.

When the purification treatment (f) for the first fluid containing the water and by-products is carried out by distillation in the presence of an organic compound, the process consists in adding an organic compound to the first fluid and in subjecting the mixture containing the first fluid and the organic compound to a distillation treatment.

This distillation process (f) can be carried out according to the standard methods of azeotropic distillation.

After the distillation (f) a first liquid phase containing the organic compound and a second liquid phase containing water freed of by-products and of any traces of organic compound can be collected as the distillation head, on the one hand, and a mixture of organic compound and of by-products can be collected as the distillation tail, on the other hand. Two different liquid phases collected as the distillation head can be separated according to the standard separation methods such as decantation. Thus, the first liquid phase containing the organic compound is recovered, on the one hand, and can be recycled into the distillation (f), just as it is or after it has been subjected to a purification treatment. On the other hand, the second liquid phase containing the water freed of by-products and of any traces of organic compound is recovered. These traces of organic compound can optionally be recovered by stripping in order to be recycled into the distillation (f). The distillation tail, which contains a mixture of organic compound and of by-products, can then also be subjected to an evaporation, optionally under vacuum, in order to recover the organic compound in purified form and to recycle it into the distillation (f).

The organic compound which can be used in the distillation step (f) can contain one or more compounds. Generally, an organic compound which has very poor miscibility with water is used.

Organic compounds which can be used for the distillation (f) of the first fluid containing the water and by-products are aliphatic or aromatic organic derivatives which can include atoms such as oxygen and/or a halogen, as well as mixtures thereof Examples which may be mentioned are alkylaromatic hydrocarbons bearing one or more alkyl groups containing from 1 to 4 carbon atoms, such as toluene, xylene, 1,3,5-trimethylbenzene, ethylbenzene and butylbenzene. Xylene is particularly preferred. The term xylene is understood to refer equally to o-, m- and p-xylenes and to mixtures thereof Mention may also be made of saturated aliphatic hydrocarbons containing from 5 to 12 carbon atoms, such as pentane, hexane, octane and decane, as well as cycloaliphatic hydrocarbons such as decalin.

When the purification treatment (f) for the first fluid containing the water and by-products is carried out by extraction using an extraction liquid, an extraction liquid which has very poor miscibility with water is generally used. The extraction liquid can contain one or more compounds.

Compounds which may be used as extraction liquid in the treatment (f) of the first fluid containing the water and by-products are aliphatic or aromatic organic derivatives which can include sulphur, phosphorous, nitrogen or oxygen atoms and/or a halogen atom. Examples which may be mentioned are trialkylphosphine oxides and 1,2-dichloropropane. The latter compound proves to be most particularly advantageous since it is formed as a by-product in the manufacturing process according to the invention. Trialkylphosphine oxides in which each of the alkyl groups contains from 2 to 20 carbon atoms, in particular from 4 to 10 carbon atoms, are particularly suitable. Trihexylphosphine oxide, trioctylphosphine oxide, (octyl, dihexyl) phosphine oxide and (hexyl, dioctyl)phosphine oxide and mixtures thereof are particularly preferred.

The process according to the invention can be carried out in a continuous, semi-continuous or batchwise manner.

The process according to the invention has the advantage of leading to a reduced volume of aqueous effluent (of from 1 to 1.5 m$^3$ of effluent per tonne of epichlorohydrin produced). The term aqueous effluent is understood to denote the first fluid containing the water and by-products produced in the distillation step (e).

It also has the advantage of resulting in a high reaction selectivity. When the process is carried out continuously, selectivities of greater than or equal to 98% can be achieved. When the process is carried out in a batchwise manner, selectivities of greater than or equal to 99% can be achieved.

This process also has the advantage of not giving rise, during the epoxidation step (a), to significant decomposition of the hydrogen peroxide into oxygen.

The example which follows is intended to illustrate the present invention without, however, limiting its scope.

EXAMPLE

The plant includes two thermostatically-controlled vertical tubular reactors mounted in cascade. A fixed bed of catalyst is placed in each reactor. Each reactor is fitted with a loop and a pump to allow recirculation of liquid over the catalyst. The temperature is homogenized by means of a cooling coil in each reactor. The volume of the catalytic bed in each reactor is 125 ml for a total volume (reactor+ recirculation loop) of 300 ml.

7.4 g of catalyst TS-1 were placed in each reactor. The reactor is fed continuously at a flow rate of 375 ml/h (337 g/h) with a solution of allyl chloride and hydrogen peroxide in methanol, (allyl chloride/$H_2O_2$=2 mol/mol; $H_2O_2$ concentration in the solution introduced=1.34 mol/kg) at a temperature of 10° C. The residence time of the reactant mixture over the catalyst is 20 minutes. The reactant mixture (allyl chloride, hydrogen peroxide and methanol) is prepared just before it is introduced, at a constant flow rate, into the top of the first reactor.

The linear throughput speed of the solution recirculating in each reactor was adjusted to 0.94 ml/min and the recirculation flow rate is about 30/h.

The test time was set on the basis of a 25% decrease in the initial activity of the catalyst in the first reactor after establishing the conditions for 1 hour.

Under these conditions and after an operating time of 6 hours, a reaction mixture containing 78 g of epichlorobydrin is recovered. The epichlorohydrin selectivity (i.e. the molar ratio between the amount of epichlorohydrin produced and the sum of the amounts of products formed) is 99.1% on the basis of the allyl chloride consumed.

This reaction mixture is subjected to an extraction treatment with o-dichlorobenzene (2.5 kg per kg of reaction mixture) in a column with plates. This device allows 99% of the epichorohydrin produced to be extracted. A first step of distillation of the extract allows a first fraction to be recovered, as a distillation head, containing the epichlorohydrin produced, the unconverted allyl chloride and traces of methanol, and a second fraction, as a distillation tail, containing the o-dichlorobenzene, which is recycled into the extraction step.

In a second distillation step, the allyl chloride and the traces of methanol are separated out, as a distillation head, after which the epichlorohydrin-based product is collected and dried in an azeotropic column. The epichlorohydrin-based product is then recovered as a gaseous phase. It contains, as chloro impurities, only 10 ppm of 1-chloro-3-methoxy-2-propanol and 35 ppm of 1,3-dichloro-2-propanol and, as non-chloro impurities, only 100 ppm of methyl glycidyl ether and 40 ppm of 2-methoxy-1-propanol.

What is claimed is:

1. A purified epichlorohydrin product produced by reaction between allyl chloride and a peroxide in water and methanol, during which reaction methyl glycidyl ether is produced in a contaminating amount, wherein said product comprises at least 99.9% by weight of epichlorohydrin; a total amount of chloro impurities of less than or equal to 150 ppm by weight and an amount of methyl glycidyl ether which is less than said contaminating amount.

2. Product according to claim 1, further comprising methyl glycidyl ether which is present in an amount of less than or equal to 250 ppm by weight.

3. Product according to claims 1 or 2, further comprising 2-methoxy-1-propanol which is present in an amount of less than or equal to 100 ppm by weight.

4. Process for manufacturing an epichlorohydrin-based product containing at least 99.9% by weight of epichlorohydrin and a total amount of chloro impurities of less than or equal to 150 ppm by weight, which comprises a) reacting allyl chloride with a peroxide compound in the presence of water, a catalyst which is a titanium silicalite, and a diluent in at least one reactor, to produce a reaction mixture comprising epichlorohydrin contaminated with an amount of methyl glycidyl ether and b) subjecting the reaction mixture of a) to a treatment to separate out the epichlorohydrin; and c) recovering a purified epichlorohydrin product with a reduced amount of methyl glycidyl ether, compared to that in said reaction mixture.

5. Process according to claim 4, in which the epichlorohydrin separation treatment (b) is carried out by extraction using an extraction solvent and in which an extract containing at least some of the extraction solvent, at least 10% of the epichlorohydrin produced, possibly an excess of allyl chloride and traces of the diluent, on the one hand, and a raffinate containing at least some of the diluent, at least some of the water, and traces of epichlorohydrin and of by-products, on the other hand, are collected after extraction in step (b).

6. Process according to claim 5, in which the extract is subjected to a distillation treatment (c) in order to separate a first fraction containing the epichlorohydrin produced, the excess allyl chloride, if any, and traces of diluent from a second fraction containing the extraction solvent, which is recycled into the extraction step (b).

7. Process according to claim 6, in which the first fraction obtained in the distillation step (c) is subjected to a distillation treatment (d) in order to remove the excess allyl chloride, if any, and the traces of diluent, which are recycled into the epoxidation step (a), and an epichlorohydrin-based product is collected and then dried in an azeotropic column.

8. Process according to claim 5, in which the raffinate obtained in the extraction step (b) is subjected to a distillation (e) in order to separate a first fluid containing the water and by-products from a second fluid containing the diluent and traces of epichlorohydrin, which are recycled into the epoxidation step (a).

9. Process according to claim 8, in which the first fluid is subjected to a purification treatment (f) in order to remove the by-products and in which the purification treatment is carried out by distillation in the presence of an organic compound or by extraction using an extraction liquid.

10. Process according to claim 4, in which the diluent is methanol and the peroxide compound is hydrogen peroxide.

11. Product according to claim 2, containing an amount of 2-methoxy-1-propanol of less than or equal to 100 ppm by weight.

12. Process according to claim 5, in which the diluent is methanol and the peroxide compound is hydrogen peroxide.

13. Process according to claim 6, in which the diluent is methanol and the peroxide compound is hydrogen peroxide.

14. Process according to claim 7, in which the diluent is methanol and the peroxide compound is hydrogen peroxide.

15. Process according to claim 8, in which the diluent is methanol and the peroxide compound is hydrogen peroxide.

16. Process according to claim 9, in which the diluent is methanol and the peroxide compound is hydrogen peroxide.

17. Epichlorohydrin-based product according to claim 1, in which the chloro impurities are by-products formed by reaction between epichlorohydrin and water or optionally the diluent.

18. Epichlorohydrin-based product according to claim 17, in which the chloro impurities are 1-chloro-2-methoxy-3-propanol, 1,3-dichloro-2-propano, 2,3-dichloropropanol and 1-chloro-2,3-dihydroxypropane.

19. Process for manufacturing an epichlorohydrin-based purified product containing at least 99.9% by weight of epichlorohydrin and a total amount of chloro impurities of less than or equal to 150 ppm by weight, selected from the group consisting of 1-chloro-2-methoxy-3-propanol, 1,3-dichloro-2-propano, 2,3-dichloropropanol 1-chloro-2,3-dihydroxypropane and admixtures thereof, which comprises a) reacting allyl chloride with a peroxide compound in the presence of water, a catalyst which is a titanium silicalite, and methanol in at least one reactor, to produce a reaction mixture comprising epichlorohydrin contaminated with an amount of methyl glycidyl ether and an amount of chloro impurities; and b) subjecting the reaction mixture of a) to a treatment to separate out the epichlorohydrin; and c) recovering a purified epichlorohydrin product with a reduced amount of methyl glycidyl ether, compared to that in said reaction mixture;

d) distilling the epichlorohydrin to reduce the amount of chloro impurities.

20. The process of claim 19, wherein the peroxide compound comprises hydrogen peroxide.

21. The process of claim 19, wherein the reacting of a) is undertaken at a temperature of less than 150° C.

22. The process of claim 19, wherein the reacting of a) is undertaken at a temperature of 0 to 120° C.

23. A purified epichlorohydrin product produced by reaction between allyl chloride and a peroxide in water and methanol, during which reaction methyl glycidyl ether and chloro impurities are produced in a contaminating amount, wherein said product comprises epichlorohydrin, chloro impurities and methylglycidyl ether, wherein the product comprises at least 99.9% by weight of epichlorohydrin; a total amount of chloro impurities of less than or equal to 150 ppm by weight and an amount of methyl glycidyl ether which is less than said contaminating amount.

24. A purified epichlorohydrin product produced by reaction between allyl chloride and a peroxide in water and methanol, during which reaction methyl glycidyl ether and chloro impurities are produced in a contaminating amount, wherein said product comprises epichlorohydrin, methylglycidyl ether, and chloro impurities selected from the group consisting of 1-chloro-2-methoxy-3-propanol, 1,3-dichloro-2-propano, 2,3-dichloropropanol 1-chloro-2,3-dihydroxypropane and admixtures thereof, wherein the product comprises at least 99.9% by weight of epichlorohydrin; a total amount of chloro impurities of less than or equal to 150 ppm by weight and an amount of methyl glycidyl ether which is less than said contaminating amount.

* * * * *